(12) United States Patent
Gaugler et al.

(10) Patent No.: US 9,702,799 B2
(45) Date of Patent: Jul. 11, 2017

(54) STATIC GEL STRENGTH TESTING

(71) Applicant: HALLIBURTON ENERGY SERVICES, INC., Houston, TX (US)

(72) Inventors: Drew H. Gaugler, Prudhoe Bay, AK (US); Ronnie G. Morgan, Waurika, OK (US); Dennis Gray, Comanche, OK (US); Sairam K. S. Pindiprolu, Pune (IN)

(73) Assignee: Halliburton Energy Services, Inc., Houston, TX (US)

( * ) Notice: Subject to any disclaimer, the term of this patent is extended or adjusted under 35 U.S.C. 154(b) by 402 days.

(21) Appl. No.: 13/894,762

(22) Filed: May 15, 2013

(65) Prior Publication Data
US 2013/0247653 A1   Sep. 26, 2013

Related U.S. Application Data

(63) Continuation-in-part of application No. 13/293,469, filed on Nov. 10, 2011, now Pat. No. 8,794,051.

(51) Int. Cl.
*G01N 11/14* (2006.01)
*G01N 33/38* (2006.01)

(52) U.S. Cl.
CPC .......... *G01N 11/14* (2013.01); *G01N 33/383* (2013.01)

(58) Field of Classification Search
CPC .......... G01N 11/14; G01N 2011/0026; G01N 2203/0094; G01N 33/28; G01N 33/30
See application file for complete search history.

(56) References Cited

U.S. PATENT DOCUMENTS

| | | | | |
|---|---|---|---|---|
| 2,953,682 A | * | 9/1960 | Frank et al. | 250/363.01 |
| 2,992,651 A | * | 7/1961 | Krofta | 137/92 |
| 3,229,506 A | * | 1/1966 | Bruss et al. | 73/54.28 |
| 3,883,359 A | | 5/1975 | Harvey | |
| 4,077,251 A | * | 3/1978 | Winter | 73/54.35 |
| 4,277,585 A | | 7/1981 | Fournel et al. | |
| 4,472,063 A | * | 9/1984 | Eickelmann | 366/129 |

(Continued)

FOREIGN PATENT DOCUMENTS

| | | |
|---|---|---|
| EP | 1124124 A2 | 8/2001 |
| EP | 1174582 A2 | 1/2002 |

(Continued)

OTHER PUBLICATIONS

Pimenova et al., "Measurement of Rheologocal Properties of Corn Stover Suspensions", Applied Biochemisry and Biotechnology, vol. 105-108, pp. 383-392, 2003.*

(Continued)

*Primary Examiner* — David A Rogers
(74) *Attorney, Agent, or Firm* — Chamberlain Hrdlicka

(57) ABSTRACT

A method of performing a static gel strength test on a composition can include placing the composition into a static gel strength test instrument, stirring the composition with at least one helical blade of the instrument, and measuring resistance to rotation between a stator and a rotor of the instrument. A static gel strength test instrument can include a rotor, and a stator having at least one helical blade. The static gel strength test instrument characterizes gelation of a composition. Another static gel strength test instrument can include a stator having at least one helical blade, and a rotor having at least one helical blade.

20 Claims, 6 Drawing Sheets

(56) References Cited

U.S. PATENT DOCUMENTS

| | | | |
|---|---|---|---|
| 4,648,264 A * | 3/1987 | Freese et al. | 73/64.41 |
| 4,653,313 A * | 3/1987 | Sabins et al. | 73/54.39 |
| 4,668,911 A | 5/1987 | Mueller | |
| 4,878,378 A * | 11/1989 | Harada | 73/54.35 |
| 5,209,108 A | 5/1993 | Shackelford | |
| 5,509,297 A * | 4/1996 | Miiller | G01D 3/022 73/1.01 |
| 5,546,791 A | 8/1996 | Meeten | |
| 5,708,197 A | 1/1998 | Todd et al. | |
| 5,789,352 A * | 8/1998 | Carpenter et al. | 507/209 |
| 6,065,330 A | 5/2000 | Freeman et al. | |
| 6,252,018 B1 | 6/2001 | Rupaner et al. | |
| 6,782,735 B2 | 8/2004 | Walters et al. | |
| 6,874,353 B2 | 4/2005 | Johnson et al. | |
| 7,712,526 B2 | 5/2010 | Morgan et al. | |
| 7,832,257 B2 | 11/2010 | Weightman et al. | |
| 7,915,356 B2 | 3/2011 | Arcella et al. | |
| 7,992,427 B2 | 8/2011 | Tonmukayakul et al. | |
| 8,230,723 B2 | 7/2012 | Moon et al. | |
| 8,266,949 B2 * | 9/2012 | Harris et al. | 73/54.32 |
| 8,347,693 B2 | 1/2013 | Pindiprolu et al. | |
| 8,794,051 B2 | 8/2014 | Morgan et al. | |
| 9,116,092 B2 | 8/2015 | Samaniuk et al. | |
| 2003/0033859 A1 | 2/2003 | Schoeb et al. | |
| 2003/0146001 A1 | 8/2003 | Hosie et al. | |
| 2003/0154772 A1 | 8/2003 | Jackson | |
| 2003/0159625 A1 * | 8/2003 | Reddy | C04B 24/163 106/719 |
| 2004/0149019 A1 | 8/2004 | Johnson et al. | |
| 2005/0132782 A1 * | 6/2005 | Wallevik | B01F 7/063 73/54.28 |
| 2005/0138991 A1 | 6/2005 | Wallevik et al. | |
| 2006/0070428 A1 | 4/2006 | Bateson et al. | |
| 2006/0081373 A1 * | 4/2006 | Santra et al. | 166/293 |
| 2007/0173412 A1 * | 7/2007 | Allin et al. | 507/224 |
| 2007/0248454 A1 | 10/2007 | Davis et al. | |
| 2008/0105040 A1 | 5/2008 | Bivens et al. | |
| 2008/0230220 A1 | 9/2008 | Morgan et al. | |
| 2010/0018294 A1 | 1/2010 | Tonmukayakul et al. | |
| 2010/0071442 A1 | 3/2010 | Moon, Jr. et al. | |
| 2010/0181070 A1 | 7/2010 | Harris et al. | |
| 2011/0061451 A1 | 3/2011 | Harris et al. | |
| 2011/0162845 A1 * | 7/2011 | Ravi et al. | 166/293 |
| 2012/0048008 A1 | 3/2012 | Pindiprolu et al. | |
| 2013/0118235 A1 | 5/2013 | Morgan | |
| 2014/0311225 A1 | 10/2014 | Morgan et al. | |

FOREIGN PATENT DOCUMENTS

| | | | |
|---|---|---|---|
| EP | 2339110 A1 | | 6/2011 |
| EP | 2867448 A1 | | 5/2015 |
| JP | 60034728 A | * | 3/1984 |
| WO | WO-2013/070382 A1 | | 5/2013 |
| WO | WO-2014/185899 A1 | | 11/2014 |

OTHER PUBLICATIONS

International Search Report with Written Opinion issued Feb. 12, 2014 for PCT Patent Application No. PCT/US13/041121, 13 pages.
Edmundo Brito-De La Fuente, et al.; "Process Viscometry of Complex Fluids and Suspensions with Helical Ribbon Agitators", The Canadian Journal of Chemical Engineering, vol. 76, dated Aug. 1998, 7 pages.
Temco, Inc.; "Rheometer for Cement and Drilling/Fracturing Fluids: Model Rheo-15", Instruction Manual, dated Aug. 13, 1996, 5 pages.
American Petroleum Institute; "Calculation of Corrosion Rates", p. 44, received Jul. 6, 2011, 1 page.
FANN; "iX77 Rheometer", production information, dated 2007, 4 pages.
P.J. Cullen, et al.; "Rotational Rheometry Using Complex Geometries", A Review, dated Nov. 28, 2002, 20 pages.
Patrice Estelle, et al; "Shear Flow Curve in Mixing Systems—A Simplified approach", Chemical Engineering Science 63, dated Aug. 22, 2008, 4 pages.
M. Elena Castell-Perez, et al.; "Simple Determination of Power Law Flow Curves using a Paddle Type Mixer Viscometer", Research Note, dated May 13, 1991, 14 pages.
Z. Kemblowski, et al.; "The Concept of a Rotational Rheometer with Helical Screw Impeller", Rheologica Acta, vol. 27: 82-91, dated 1998, 12 pages.
C. Salas-Bringas, et al.; "Time Variations and Calibration of a Screw Type Process Rheometer", Applied Rheology vol. 20, Issue 3, dated Dec. 16, 2009, 11 pages.
Pavla Novotna, et al.; "Use of Helical Ribbon Mixer for Measurement of Rheological Properties of Fruit Pulps", Czech J. Food Sci., vol. 9, No. 4: 148-153, dated 2001, 6 pages.
New Mexico Tech; "Well Design PE 413", Oil well cementing power point presentation, dated Spring 2012, 29 pages.
Society of Petroleum Engineers; "Interrelationship Between Critical Cement Properties and Volume Changes During Cement Setting", SPE 20451, dated Sep. 23-26, 1990, 14 pages.
I. Eriksson, et al.; "Evaluation of a Helical Ribbon Impeller as a Viscosity Measuring Device for Fluid Foods with Particles", dated May 21, 2002, 6 pages.
M.S. Tamura, et al.; "Evaluation of the Helical Screw Rheometer as an On-line Viscometer", Journal of Food and Science, vol. 54, No. 2, research note, dated 1989, 2 pages.
James F. Steffe; "Rheological Methods in Food Process Engineering", Second Edition, dated Jun. 1996, 428 pages.
Halliburton; "Rheology", research presentation, dated Feb. 27, 2001, 23 pages.
Fann Instrument Company; "Multiple Analysis Cement System MACS II", company brochure, dated 2011, 4 pages.
J.I. Briggs, et al.; "Mixer Viscometer Constant (k') for the Brookfield Small Sample Adapter and Flag Impeller", manuscript, dated Aug. 30, 1996, 7 pages.
A.P. Omura, et al.; "Mixer Viscometry to Characterize Fluid Foods with Large Particles", manuscript, dated Mar. 17, 2003, 11 pages.
Institution of Chemical Engineers; "Mixing with Hellical Ribbon Impellers: Effect of Highly Shear Thinning Behavior and Impeller Geometry", Trans IChemE, vol. 75, Part A, dated Jan. 1997, 8 pages.
M.S. Tamura, et al.; "Performance of the Helical Screw Rheometer for Fluid Food Suspensions", Journal of Food and Science, vol. 58, No. 5, dated 1993, 6 pages.
David L. Sutton; "Annular Gas Flow Theory and Prevention Methods Described New Evaluation for Annular Gas-Flow Potential", Oil & Gas Journal, datedDec. 10-17, 1984, 11 pages.
Sabins, Fred L.; "Transition Time of Cement Slurries Between the Fluid and Set States", SPE 9285, dated Dec. 1982, 8 pages.
Sabins, Fred L.; "The relationship of Thickening Time, Gel Strength of Oilwell Cements", SPE 11205, dated Mar. 1986, 10 pages.
Journal of Food Engineering; "Estimation and prediction of shear rate distribution as a model mixer", technology paper, dated Nov. 11, 1999, 14 pages.
M. Elena Castell-Perez; "Evalutating Shear Rates for Power Law Fluids in Mixer Viscometry", technical paper, dated Sep. 11, 1990, 14 pages.
I. Eriksson; "Evaluation of a Helical Ribbon Impeller as a Viscosity Measuring Device for Fluid Foods with Particles", technical paper, dated May 21, 2002, 6 pages.
T.A. Glen III and C.R. Daubert; "A Mixer Viscometry Approach for Blending Devices", Journal of Food Process Engineering, vol. 26, pp. 1-16, dated 2003, 16 pages.
Guillaume Delaplace et al.; "A New Expression of the Ks Factor for Helical Ribbon Agitators", The Canadian Journal of Chemical Engineering, vol. 78, pp. 393-394, dated Apr. 2000, 2 pages.
C. Salas-Bringas et al.; "A New On-Line Process Rheometer for Highly Viscous Food and Animal Feed Materials", Journal of Food Engineering, vol. 79, pp. 383-391, dated 2007, 9 pages.
Voula Vlachou et al.; "A New Tool for the Rheometric Study of Oil Well Cement Slurries Other Settling Suspensions", from the Cement and Concrete Research, vol. 30, pp. 1551-1557, dated 2000, 7 pages.

(56) References Cited

OTHER PUBLICATIONS

J. L. Valverde et al.; "An Improved Method for Determining Rheological Parameters of Suspension: Statistical Approach", from the Institution of Chemical Engineers, vol. 75, Part A, pp. 784-791, dated Nov. 1997, 8 pages.
Magdalena S. Tamura et al.; "Analysis of the Helical Screw Rheometer for Fluid Food", Journal of Food Process Engineering 16, pp. 93-126, dated 1993, 34 pages.
Wikipedia; "Archimedes' Screw", from the free online encyclopedia, last modified on Oct. 31, 2011, 4 pages.
K. P. Lai et al.; "Average Shear Rates in the Rapid Visco Analyser (RVA) Mixing System", Note from the American Association of Cereal Chemists, Inc. vol. 77, No. 6, pp. 714-716, dated 2000, 3 pages.
P. Guerin et al.; "Characterization of Helical Impellers by Circulation Times", The Canadian Journal of Chemical Engineering, vol. 62, pp. 301-309, dated Jun. 1984, 9 pages.
L. Zumalacarregui et al.; "Comparison Between Models Used in the Determination of the Rheological Parameters of Suspensions with Helical Screw Impeller", from the Institution of Chemical Engineers, vol. 78, Part A, pp. 419-424, dated Apr. 2000, 6 pages.
T. J. Akroyd et al.; "Continuous On-Line Rheological Measurements for Rapid Settling Slurries" article from Minerals Engineering, vol. 16, pp. 731-738, dated 2003, 8 pages.
T. J. Akroyd et al.; "Continuous Rheometry for Industrial Slurries", from the Experimental Thermal and Fluid Science, vol. 27, pp. 507-514, dated 2003, 8 pages.
T. J. Akroyd et al.; "Continuous Rheometry for Industrial Slurries", from the Department of Chemical Engineering at the 14th Australasian Fluid Mechanics Conference, dated Dec. 10-14, 2001, 4 pages.
J.P. Guillemin et al.; "Development of a New Mixing Rheometer for Studying Rheological Behavior of Concentrated Energetic Suspensions", from the Journal of Non-Newtonian Fluid Mechanics, vol. 151, pp. 136-144, dated 2008, 9 pages.
K.L. Mackey et al.; "Effects of Shear-Thinning Behavior on Mixer Viscometry Techniques", from the Journal of Texture Studies, vol. 18, pp. 231-240, dated 1987, 10 pages.
Office Action issued Dec. 4, 2013 for U.S. Appl. No. 13/293,469, 13 pages.
American Petroleum Institute, "Section 8: Thickening Time Tests (Specification Test)", article, undated, pp. 22-28, 7 pages.
Lord et al., "Real-Time Fracturing Fluid Rheology Measurements with the Helical Screw Rheometer", SPE 19734, Oct. 1989, 8 pages.
Lord, D.L., "Helical Screw Rheometer: A New Tool for Stimulation Fluid Evaluation", SPE 18213, Oct. 1998, 7 pages.
Mackey et al., "Effects of Shear-Thinning Behavior on Mixer Viscometry Techniques", Journal Article No. 12280, Apr. 1, 1987, 18 pages.
Thesing, A., "New Device for Rheology Measurements of Proppant-Laden Fluids with the Fann 50 Viscometer", SPE 58759, Feb. 2000, 10 pages.
Schatzmann, M, et al., "Rheometry for large-particulated fluids: analysis of the ball measuring system and comparison to debris flow rheometry", Rheologica Acta, Springer-Verlag vol. 48, No. 7, (Apr. 23, 2009), 715-733.
Zubieta, Mikel, et al., "A numerical method for determining the shear stress of magnetorheological fluids using the parallel-plate measuring system", Rheologica Acta, Springer-Verlag vol. 48, No. 1, (Oct. 31, 2008), 89-95.
U.S. Appl. No. 14/322,823, filed Jul. 2, 2014, Combined Rheometer/Mixer Having Helical Blades and Methods of Determining Rheological Properties of Fluids.
"Application Serial No. 13884923.7, Office Action mailed Mar. 12, 2015", 3 pgs.
"Canadian Application Serial No. 2,854,491, Office Action mailed Jun. 26, 2015", 5 pgs.
"European Application Serial No. 12847895.5, Extended European Search Report mailed Mar. 10, 2015", 9 pgs.
"European Application Serial No. 12847895.5, Office Action mailed Mar. 27, 2015", 1 pg.
"European Application Serial No. 12847895.5, Response filed Aug. 21, 2015 to Office Action mailed Mar. 27, 2015", 9 pgs.
"European Application Serial No. 13884923.7, Response filed Sep. 8, 2015 to Office Action mailed Mar. 12, 2015", 9 pgs.
"International Application Serial No. PCT/US2012/060085, International Preliminary Report on Patentability dated", 6 pgs.
"International Application Serial No. PCT/US2012/060085, International Search Report mailed Mar. 18, 2013", 7 pgs.
"International Application Serial No. PCT/US2012/060085, Written Opinion mailed Mar. 18, 2013", 5 pgs.
"International Application Serial No. PCT/US2013/041121, International Preliminary Report on Patentability mailed Nov. 26, 2015", 10 pgs.
"International Application Serial No. PCT/US2013/041121, International Preliminary Report on Patentability dated Nov. 17, 2015", 9 pgs.
"International Application Serial No. PCT/US2013/041121, International Search Report mailed Feb. 12, 2014", 3 pgs.
"International Application Serial No. PCT/US2013/041121, Written Opinion mailed Feb. 12, 2014", 8 pgs.
"U.S. Appl. No. 13/293,469, Amendment filed Feb. 21, 2014 in response to Non Final Office Action mailed Dec. 4, 2013", 14 pgs.
"U.S. Appl. No. 13/293,469, Notice of Allowance mailed Mar. 25, 2014", 5 pgs.
"U.S. Appl. No. 13/293,469, Response filed Oct. 2, 2013 to Restriction Requirement mailed Sep. 18, 2013", 2 pgs.
"U.S. Appl. No. 13/293,469, Restriction Requirement mailed Sep. 18, 2013", 5 pgs.
Sairam, P. K. S., et al., "A Combined Mixer Designer with Helical Blades to Probe Rheology of Complex Oilfield Slurries and Pastes". SPE 159112. SPETT 2012 Energy Conference and Exhibition held in Port of Spain, Trinidad, Jun. 11-13, 2012, (2012), 1-21.
"U.S. Appl. No. 14/322,823, Non Final Office Action mailed Sep. 8, 2016", 11 pgs.
"Australian Application Serial No. 2013389300, First Examiner Report mailed Jul. 22, 2016", 4 pgs.
"Canadian Application Serial No. 2,885,174, Response filed Sep. 7, 2016 to Office Action mailed Apr. 11, 2016", 16 pgs.

* cited by examiner

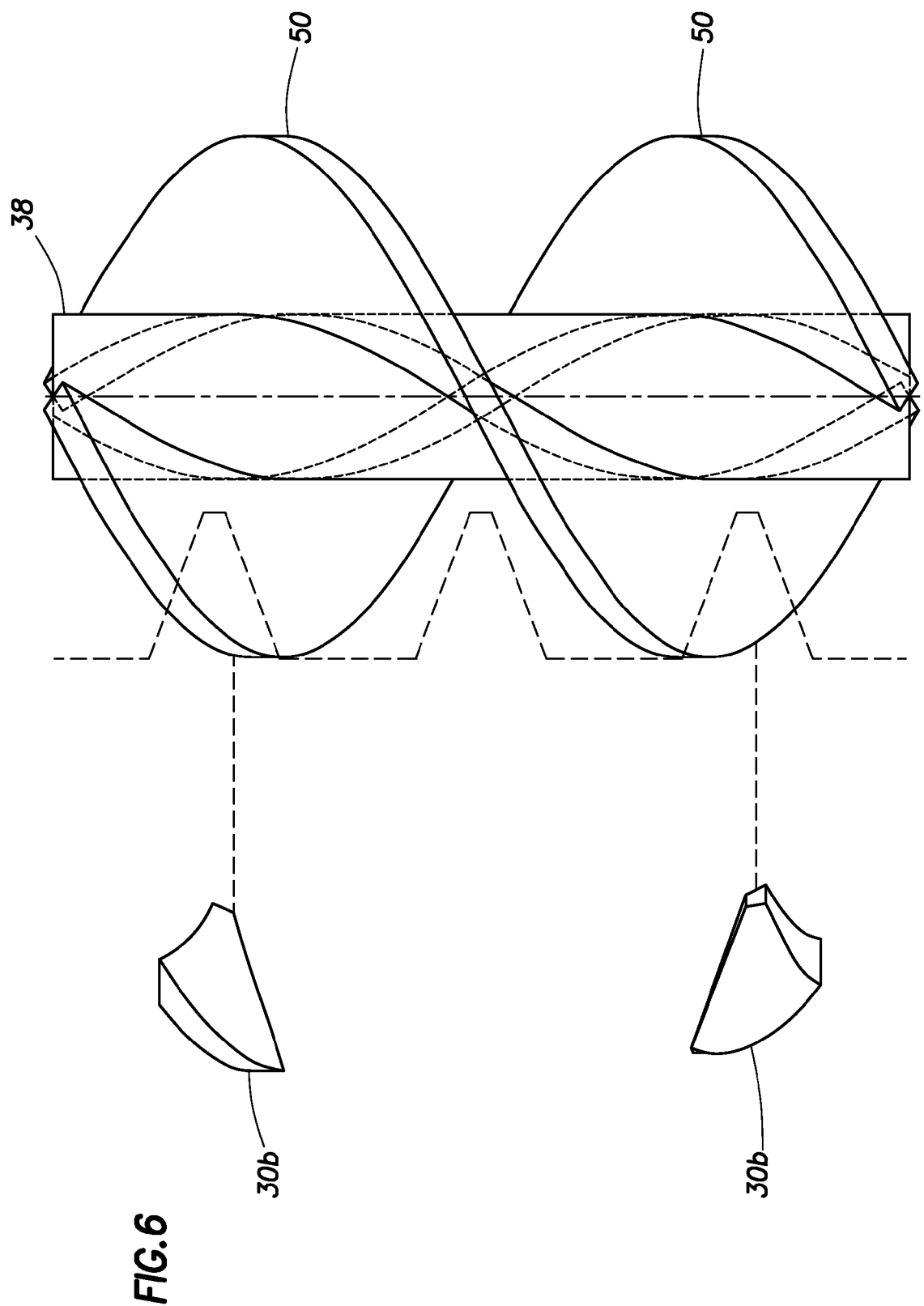

STATIC GEL STRENGTH TESTING

CROSS-REFERENCE TO RELATED APPLICATION

This application is a continuation-in-part of prior application Ser. No. 13/293,469, filed 10 Nov. 2011, the entire disclosure of which is incorporated herein by this reference.

BACKGROUND

This disclosure relates generally to testing methods and apparatus and, in an example described below, more particularly provides improvements in static gel strength testing.

For prospective cementing operations to be performed in subterranean wells, static gel strength testing is useful to determine how a particular cement composition will perform in downhole conditions. In particular, a static gel strength test can provide information as to how long it will take the cement composition to develop sufficient gel strength to prevent gas percolation through the cement composition.

This information is very useful because, while the cement composition is developing gel strength, its ability to transmit pressure is typically decreasing, thereby decreasing hydrostatic pressure in an annulus (e.g., between a wellbore and a casing or liner) in which the cement composition has been placed. Unless appropriate measures are taken, this decreased hydrostatic pressure could allow gas in an earth formation exposed to the annulus to enter the annulus and percolate upward through the not-yet-hardened cement composition—a situation to be avoided.

Thus, it will be appreciated that improvements are continually needed in the art of static gel strength testing. Such improvements can be useful in testing the static gel strength of cement compositions, or of other slurries, fluids, gels, substances, etc., which develop gel strength.

BRIEF DESCRIPTION OF THE DRAWINGS

FIG. 6 is a representative side view of a blank and stator blades which may be used in the instrument.

DETAILED DESCRIPTION

For the purpose of facilitating industry-wide collaboration and advancements regarding this very important technology, the American Petroleum Institute (API) has developed standards for testing static gel strength (nominally, the gel strength developed after a cement composition has been appropriately placed in a well). According to an API standard well known to those skilled in the art (e.g., API RP 10B-6), a transition time is measured between a gel strength of 100 lb/100 ft$^2$ and a gel strength of 500 lb/100 ft$^2$. Typically, it is desired for the transition time to be less than 30 minutes, and preferably the transition time should be less than 15 minutes.

During the static gel strength test, the cement composition is heated, pressurized and stirred, in order to at least approximate downhole conditions to which the cement composition will be exposed. For example, the cement composition may be stirred at 150 rpm while being heated and pressurized, and then the cement composition may be stirred at a much slower rate (e.g., 0.2 degrees/minute or other) while a temperature of the composition is increased or decreased to an expected downhole temperature at a location where the composition is to be placed. The cement composition develops gel strength while being stirred at this much slower rate, and the transition time is measured.

The foregoing described static gel strength tests may be performed using any suitable rotating-type static gel strength apparatus. For example, a MACS-II™ test instrument, available from Fann Instrument Company of Houston, Tex., USA, is commonly used for such static gel strength tests.

The present inventors have discovered that, unfortunately, it is often the case that a rotor paddle of the test instrument fails to adequately stir the cement composition as it develops gel strength. Instead, a "plug" of the gelling composition gradually forms within a framework of the paddle, and this "plug" rotates with the paddle relative to a stator cup of the instrument. When the cup and paddle are disassembled following a test, a relatively thin layer of the composition is found between the stator cup and the rotor paddle (and its associated "plug").

As a result, the gel strength measurements made during the test when the "plug" forms are inaccurate. Although it is generally possible to estimate what the gel strength measurements would have been had the "plug" not formed (for example, by extrapolating the measurements made prior to the "plug" forming), actual accurate gel strength measurements would be far preferable to such estimates.

Figure 1:
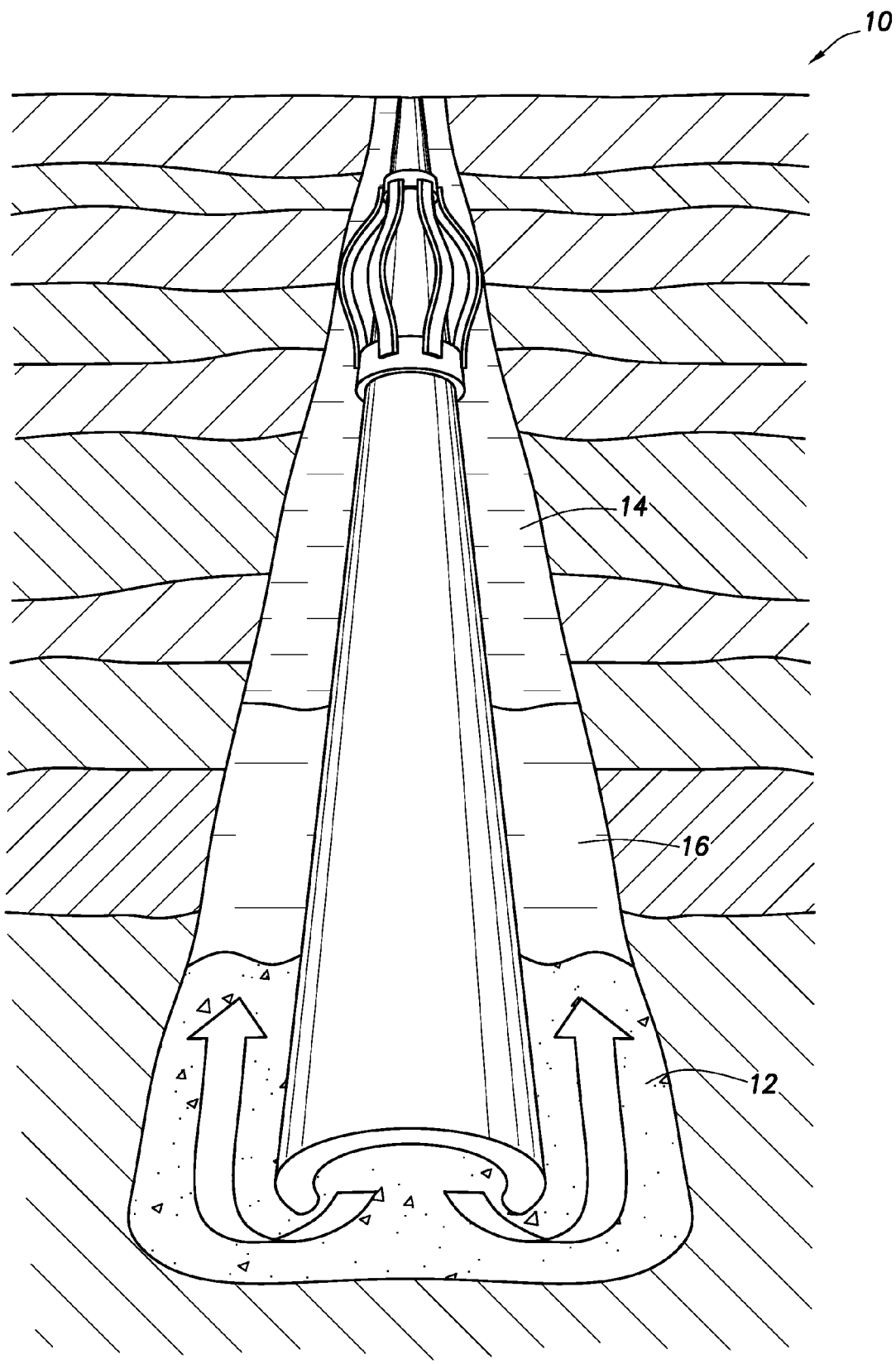
FIG. 1 is a representative partially cross-sectional view of a well system and associated method which can benefit from the principles of this disclosure.

Representatively illustrated in FIG. 1 is a well system 10 and associated method which can benefit from the principles of this disclosure. In the well system 10, various fluids 14, slurries, spacers 16, barriers, gels, etc., can be flowed through various flowpaths in a well, and it is beneficial to be able to accurately characterize each of these, particularly at downhole conditions, so that well operations can be most efficiently, safely, expeditiously and effectively performed.

The description below focuses on static gel strength testing for a cement composition 12 used in the well system 10. The term "cement" herein indicates a composition typically comprising mostly Portland cement and water, with various additives. However, it is to be clearly understood that the scope of this disclosure is not limited to use only with the cement composition 12.

In the FIG. 1 example, the composition 12 is flowed into an annulus between a tubular string (such as, a casing or liner string) and a drilled wellbore. When hardened, the composition 12 will seal off the annulus and prevent fluid migration between formations penetrated by the wellbore, protect the tubular string, and serve various other purposes. In other examples, the composition 12 could be used to plug an interior of the tubular string. Thus, the scope of this disclosure is not limited to any particular purpose for which the composition 12 is used.

Figure 2:
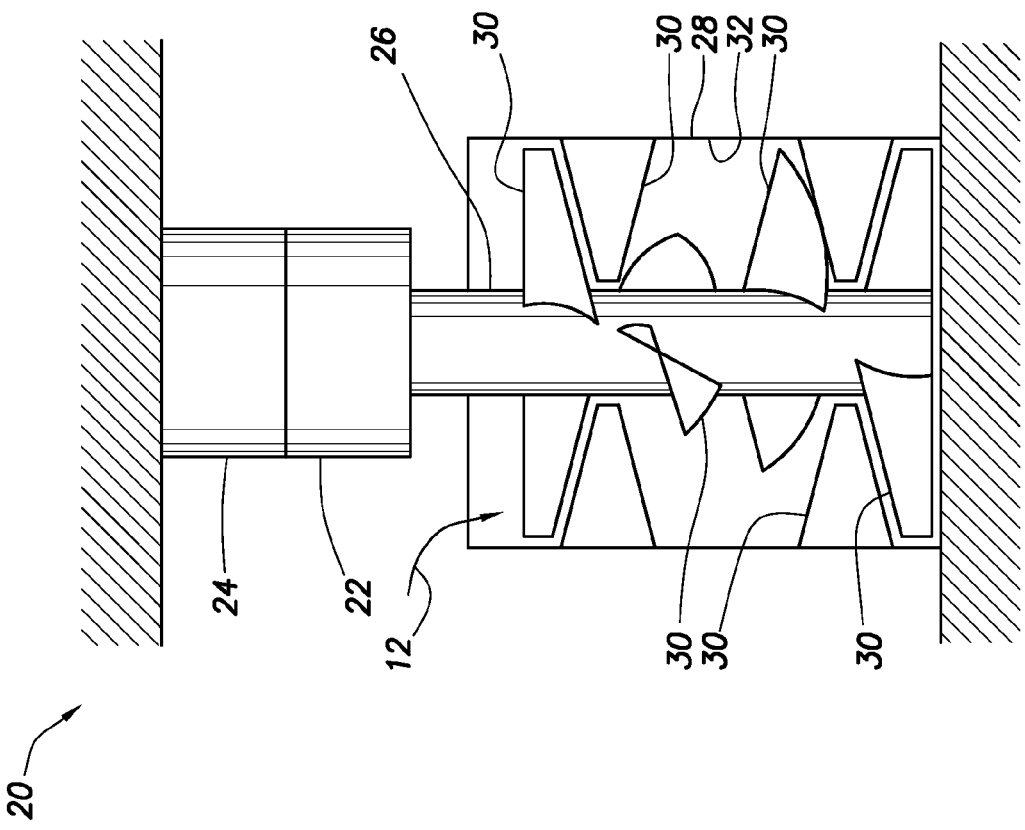
FIG. 2 is a representative partially cross-sectional view of a static gel strength test instrument which can embody principles of this disclosure.

One example of a static gel strength test instrument 20 which can embody the principles of this disclosure is representatively and schematically illustrated in FIG. 2. For clarity of illustration and explanation, FIG. 2 does not depict pumps or heaters used to pressurize and heat the composition 12, but preferably the instrument 20 does include such pump(s) and heater(s).

A suitable static gel strength test instrument which may be modified for use as described herein is the MACS-II™ instrument mentioned above. However, the scope of this disclosure is not limited to use or modification of any particular type of static gel strength test instrument.

In this example, the instrument 20 includes a motor 22, a torque sensor 24, a rotor 26 and a stator 28. The motor 22 rotates the rotor 26 relative to the stator 28, and the torque sensor 24 measures torque due to shearing of the composition 12 in the instrument 20.

However, in other examples, other configurations of instruments may be used, static gel strength of other compositions may be investigated, etc. Therefore, it should be understood that the principles of this disclosure are not limited to the instrument 20 described herein and depicted in the drawings.

Figure 3:
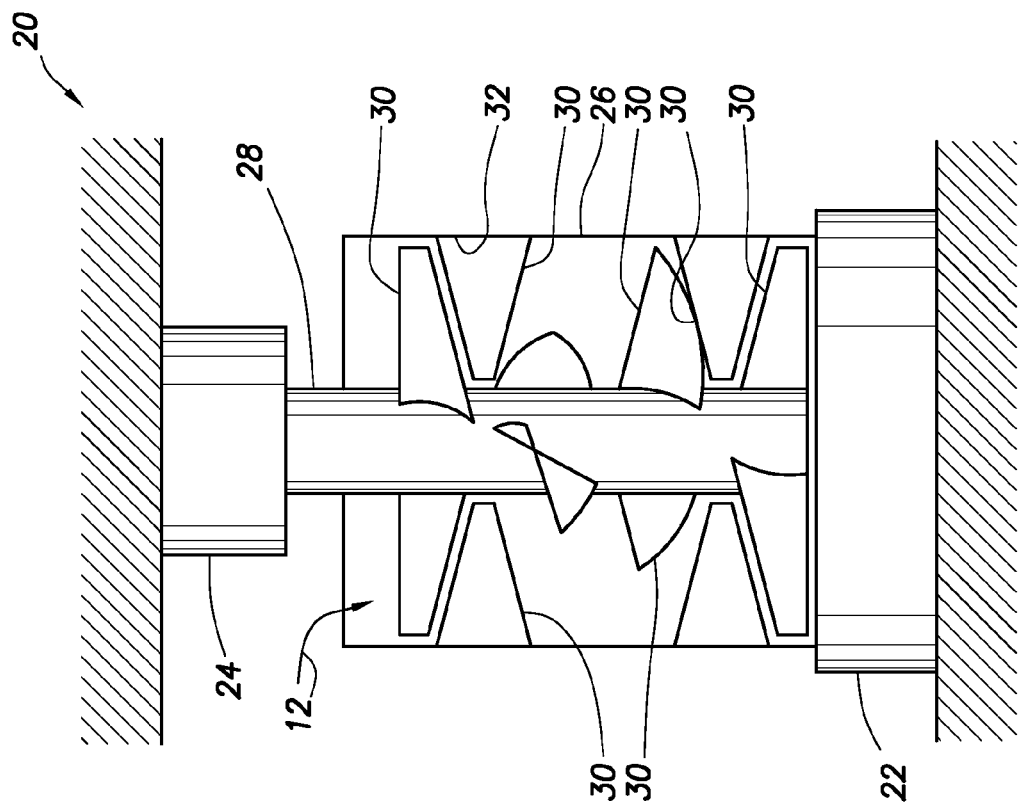
FIG. 3 is a representative partially cross-sectional view of another configuration of the instrument.

One example of another configuration of the instrument 20 is representatively illustrated in FIG. 3. In this example, the rotor 26 serves as a receptacle for the composition 12, and is rotated by the motor 22 positioned beneath the rotor.

In contrast, the FIG. 2 configuration has the stator 28 serving as a receptacle for the composition 12, with the rotor 26 being rotated by the motor 22 positioned above the rotor. This demonstrates that a variety of differently configured instruments can incorporate the principles of this disclosure, and those principles are not limited to the details of any specific examples described herein.

One feature of the instrument 20 as depicted in FIGS. 2 & 3 is that helical blades 30 are provided on the rotor 26, and on the stator 28. The helical blades 30 on the rotor 26 effectively homogenize (or at least maintain homogenization of) the composition 12, in part by ensuring that a volume of the composition at a bottom of the receptacle is urged upward toward a top of the receptacle.

Referring to FIG. 3, the helical blades 30 on the stator 28 are configured so that they intermesh with the blades on the rotor 26, and the composition 12 is sheared in a space or gap between the blades. Preferably, the gap between the blades 30 is constant along the length of the gap, to thereby provide for consistent shearing of the composition 12 between the blades. Minimal variation in the gap between the blades 30 could be present, but preferably not to an extent which unacceptably degrades the resulting measurements.

In a method of performing static gel strength tests on the composition 12, the composition is first dispensed into the receptacle, and the rotor 26 is rotated relative to the stator 28 by the motor 22. The rotation of the rotor 26, in conjunction with the helical shapes of the blades 30 effectively homogenizes the composition 12 (or at least maintains homogenization of the composition).

Note that, in the FIG. 2 configuration, the blades 30 on the rotor 26 are axially spaced apart into separate flights, with the flights being separated by the blades on the stator 28. The blades 30 on the stator 28 are helically spaced apart on an inner generally cylindrical surface 32 of the stator. Of course, other configurations of elements in the instrument 20 may be used, in keeping with the scope of this disclosure.

Preferably, the blades 30 on the stator 28 have the same shape and curvature as the blades on the rotor 26, so that the gap between the blades is uniformly consistent as one blade displaces past another, thereby preventing interference between the blades, but providing for uniform intermeshing. One method of producing such complementarily shaped blades 30 is representatively illustrated in FIGS. 4-6, for the instrument 20 of FIG. 2, but it should be understood that this is merely one example of how the blades could be produced, and other methods may be used in keeping with the scope of this disclosure.

For clarity in the description below, the blades on the rotor 26 are indicated with reference number 30a, and the blades on the stator 28 are indicated with reference number 30b, it being understood that in other examples the specific blades could be on different ones of the rotor and stator, the blades could be differently configured, etc.

Figure 5:
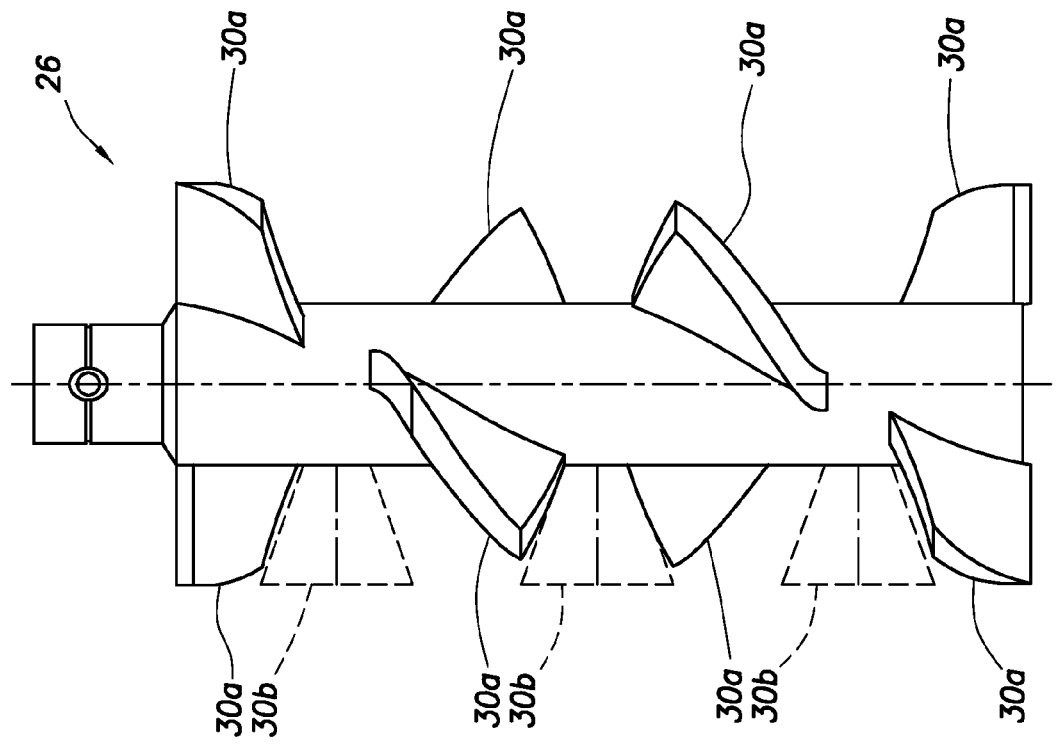
FIG. 5 is a representative side view of the rotor.
Figure 4:
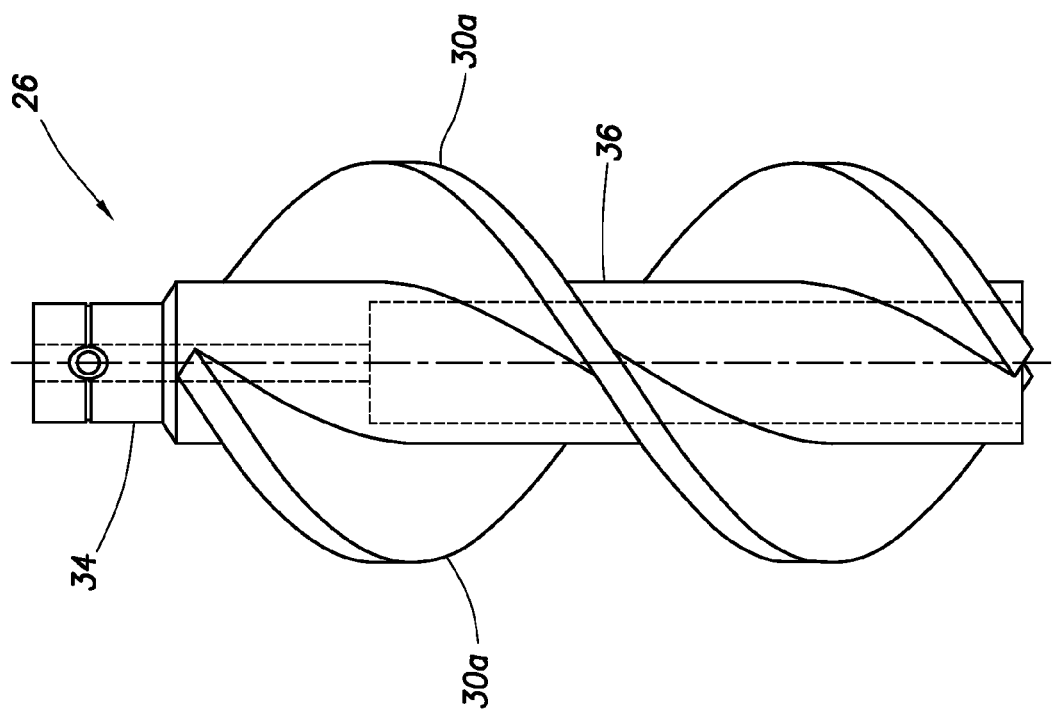
FIG. 4 is a representative side view of a blank for a rotor which may be used in the instrument.

In the example of FIGS. 4-6, the rotor 26 begins as a cast or molded blank 34 having double helix blades 30a formed thereon. As depicted in FIG. 4, the blades 30a extend outwardly from a generally cylindrical surface 36 on the rotor 26. In other examples, the blades 30a could extend inwardly, the blades could extend from a non-cylindrical origin, different numbers of blades may be used, etc.

In FIG. 5, the rotor 26 is representatively illustrated after material has been removed from the blades 30a to accommodate the blades 30b on the stator 28. Note that, in this example, the chosen peripheral shape of the blades 30b is trapezoidal (in lateral projection), to provide a desired length of a desired gap between the blades 30a,b for shearing the fluids. In other examples, different shapes (e.g., rectangular, circular, polygonal, curved, combinations of shapes, etc.) of the blades 30b may be used.

As depicted in FIG. 5, the blades 30a are axially spaced apart along the rotor in four sets of flights. In other examples, more or fewer sets of flights may be used, as desired.

In FIG. 6, it may be seen that the blades 30b for the stator 28 are cut from another blank 38 having a double helix formed thereon, similar to the double helix blades 30a on the blank 34 of FIG. 4. In this technique, the trapezoidal shape is cut from the helixes 50 on the blank 38, thereby yielding multiple blades 30b which have substantially the same helical pitch (slope) and curvature as the blades 30a on the rotor 26.

Note that it is not necessary for the blank 38 to have a double helix formed thereon. Any number of helixes may be used in keeping with the scope of this disclosure. Indeed, the blades 30b could be formed by casting, molding, etc., and without cutting them from a helix, if desired.

Figure 7:
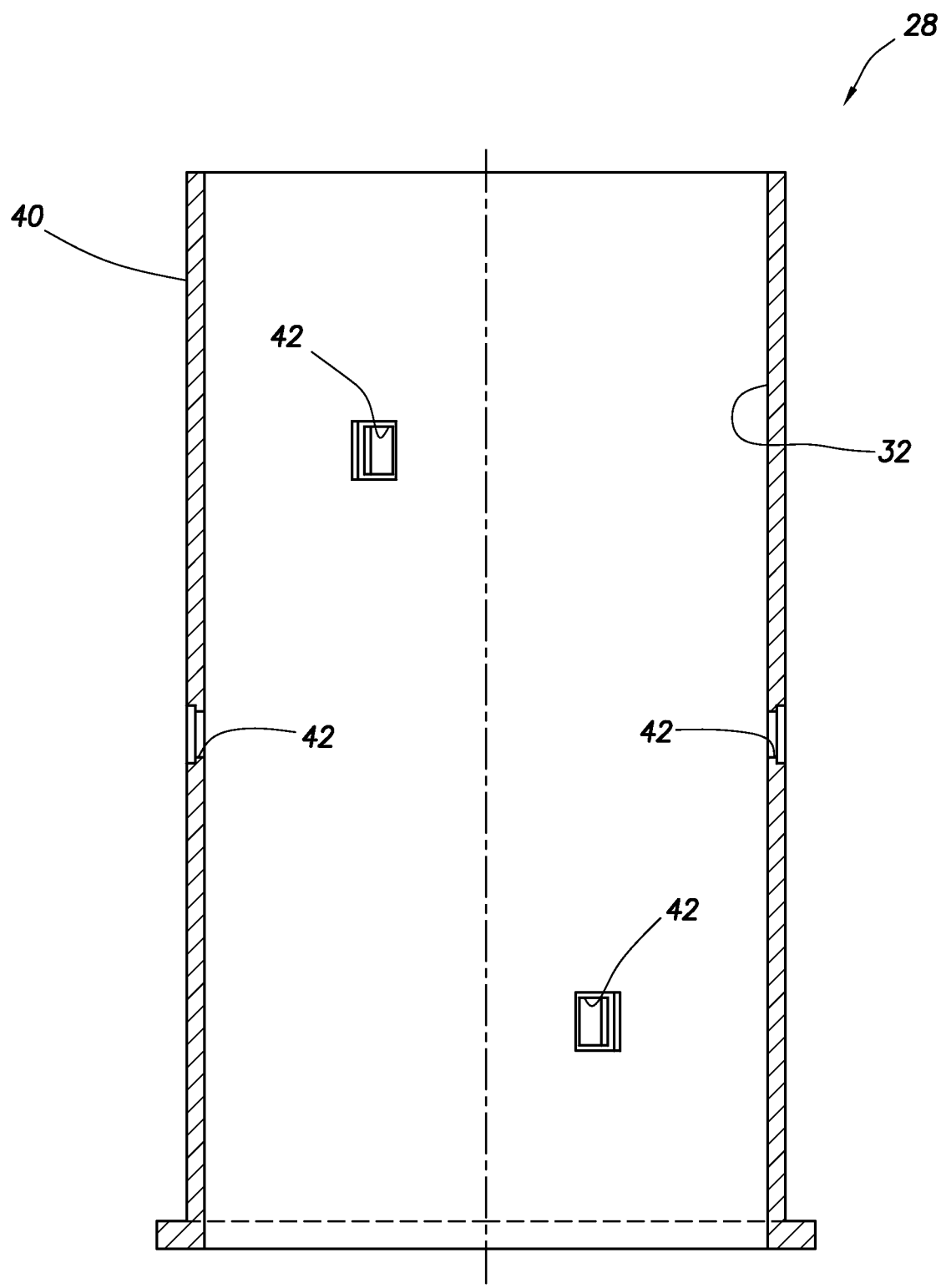
FIG. 7 is a representative cross-sectional view of a receptacle which may be used in the instrument.

Referring additionally now to FIG. 7, a receptacle 40 of the stator 28 is representatively illustrated. The receptacle 40 is provided with a series of opposing recesses 42 which are helically spaced apart along the inner cylindrical surface 32 of the receptacle.

The recesses 42 are used in this example to position the blades 30b on the stator 28. In other examples, the blades 30b could be otherwise positioned, configured or arranged.

Figure 8:
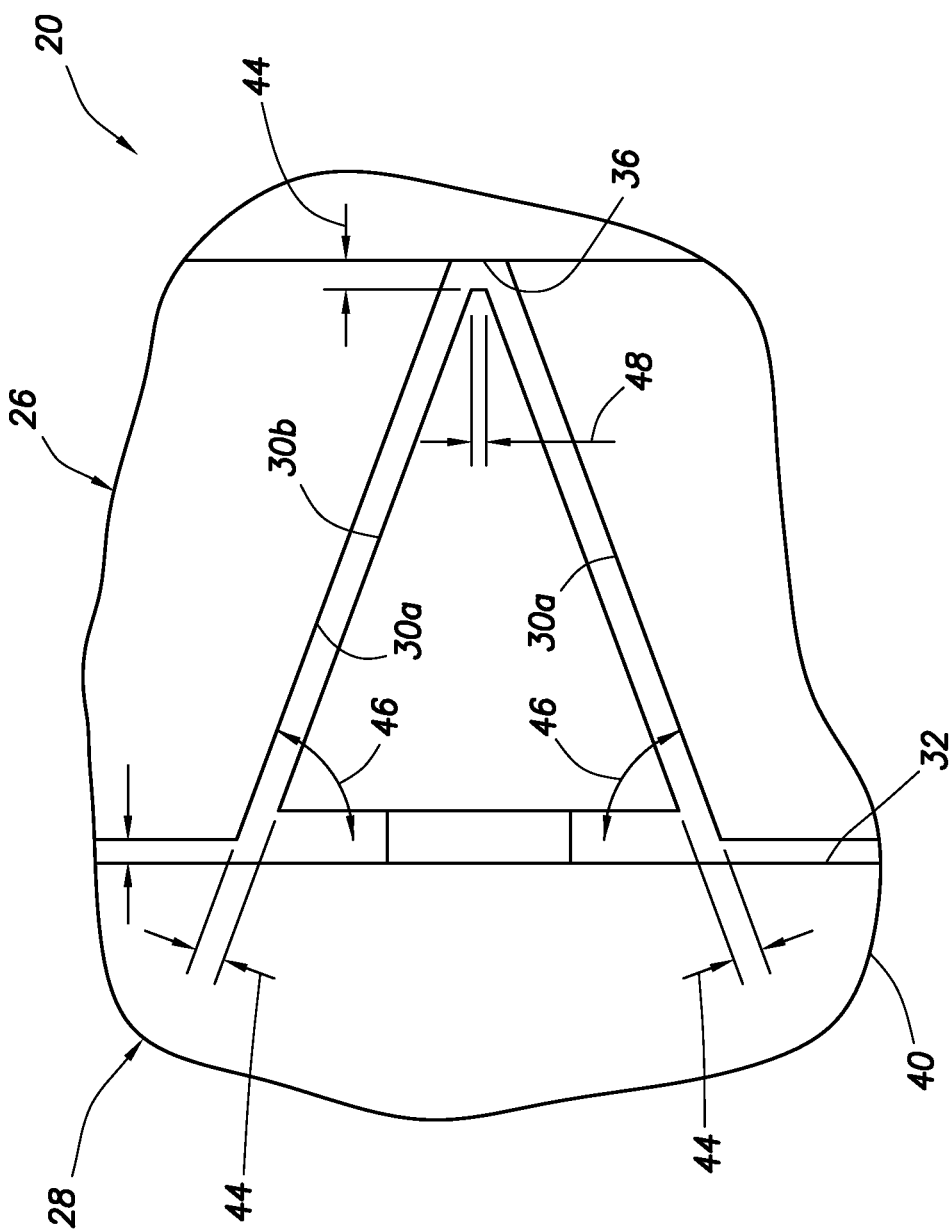
FIG. 8 is a representative side view of a consistent gap between rotor and stator blades in the instrument.

Referring additionally now to FIG. 8, an enlarged scale representative view of the blades 30a,b in the instrument 20 is illustrated in lateral projection. The blades 30a,b are depicted in FIG. 8 as if "flattened" laterally, so that the blade 30b has its trapezoidal perimeter, and the blades 30a are axially separated by trapezoidal cutouts, as in the example of FIGS. 5 & 6. However, it will be appreciated that, in this example, the blades 30a,b are actually helical in shape.

Preferably, a gap 44 between the blades 30a,b is constant, or at least substantially consistent, so that the composition 12 is sheared between the blades consistently. However, some variation in the gap 44 may be permitted, if desired.

In one example, an instrument 20 can have a consistent gap 44 of 0.150 in. (~3.8 mm) between the blades 30a,b and a base angle 46 of 70 degrees, with a tip width 48 on the blade 30b of 0.090 in. (~2.3 mm). Using this example, the cement composition 12 can be subjected to a static gel strength test, without a "plug" forming in a framework of the rotor 26. Indeed, in situ homogenization can be efficiently carried out, if desired, thereby enabling accurate "mix while measure" techniques in which the composition 12 is mixed and homogenized in the instrument 20 prior to performing the static gel strength test per se.

It may now be fully appreciated that the above disclosure provides significant advancements to the art of static gel strength testing. In examples described above, a composition can be tested for static gel strength, without a "plug" forming within a framework of a paddle/rotor of a static gel strength test instrument, but instead maintaining homogenization of the composition during the test, so that accurate static gel strength measurements can be obtained.

A method of performing a static gel strength test on a composition 12 is provided to the art by the above disclosure. In one example, the method can include: placing the composition 12 into a static gel strength test instrument 20; stirring the composition 12 with at least one helical blade 30 of the instrument 20; and measuring resistance to rotation between a stator 28 and a rotor 26 of the instrument 20.

The resistance to rotation measurement may be made by sensing torque applied to the rotor 26, measuring deflection of a biasing device which resists rotation of the stator 28, etc. The scope of this disclosure is not limited to any particular technique for measuring resistance to rotation of the rotor 26 relative to the stator 28.

The stator 28 may comprise the helical blade 30. Alternatively, or in addition, the rotor 26 may comprise the helical blade 30.

In one example described above, the at least one helical blade 30 comprises at least one first helical blade 30a on the stator 28 and at least one second helical blade 30b on the rotor 26. The first helical blade 30a may be spaced apart from the second helical blade 30b by a substantially consistent gap 44.

If multiple helical blades 30 are used, the blades 30 can be helically spaced apart on a cylindrical surface 32 of the stator 28.

If multiple helical blades 30 are used, the blades 30 can be axially spaced apart on the rotor 26.

A static gel strength test instrument 20 is also described above. In one example, the instrument 20 can include a rotor 26, and a stator 28 having at least one first helical blade 30a. The static gel strength test instrument 20 characterizes gelation of a composition 12.

Another static gel strength test instrument 20 can include a stator 28 having at least one first helical blade 30a, and a rotor 26 having at least one second helical blade 30b. However, it is not necessary in keeping with the scope of this disclosure for both of the rotor 26 and stator 28 to comprise helical blades 30.

Although various examples have been described above, with each example having certain features, it should be understood that it is not necessary for a particular feature of one example to be used exclusively with that example. Instead, any of the features described above and/or depicted in the drawings can be combined with any of the examples, in addition to or in substitution for any of the other features of those examples. One example's features are not mutually exclusive to another example's features. Instead, the scope of this disclosure encompasses any combination of any of the features.

Although each example described above includes a certain combination of features, it should be understood that it is not necessary for all features of an example to be used. Instead, any of the features described above can be used, without any other particular feature or features also being used.

It should be understood that the various embodiments described herein may be utilized in various orientations, such as inclined, inverted, horizontal, vertical, etc., and in various configurations, without departing from the principles of this disclosure. The embodiments are described merely as examples of useful applications of the principles of the disclosure, which is not limited to any specific details of these embodiments.

The terms "including," "includes," "comprising," "comprises," and similar terms are used in a non-limiting sense in this specification. For example, if a system, method, apparatus, device, etc., is described as "including" a certain feature or element, the system, method, apparatus, device, etc., can include that feature or element, and can also include other features or elements. Similarly, the term "comprises" is considered to mean "comprises, but is not limited to."

Of course, a person skilled in the art would, upon a careful consideration of the above description of representative embodiments of the disclosure, readily appreciate that many modifications, additions, substitutions, deletions, and other changes may be made to the specific embodiments, and such changes are contemplated by the principles of this disclosure. For example, structures disclosed as being separately formed can, in other examples, be integrally formed and vice versa. Accordingly, the foregoing detailed description is to be clearly understood as being given by way of illustration and example only, the spirit and scope of the invention being limited solely by the appended claims and their equivalents.

What is claimed is:

1. A method of performing a static gel strength test on a composition; the method comprising:
    placing the composition into a static gel strength test instrument having a stator and a rotor;
    stirring the composition with helical blades helically spaced apart on the stator; and
    measuring resistance to rotation between the stator and the rotor of the instrument.

2. The method of claim 1, wherein measuring the resistance comprises sensing torque applied to the rotor by measuring deflection of a biasing device.

3. The method of claim 1, wherein the rotor comprises helical blades.

4. The method of claim 1, wherein the rotor comprises helical blades, and wherein the method further comprises shearing the composition in a space between the helical blades of the stator and the helical blades of the rotor.

5. The method of claim 1, wherein the rotor comprises helical blades spaced apart from the helical blades of the stator by a substantially consistent gap.

6. The method of claim 1, wherein the helical blades are helically spaced apart on a cylindrical surface of the stator.

7. The method of claim 1, wherein the rotor comprises helical blades axially spaced apart on the rotor.

8. A static gel strength test instrument, comprising:
    a rotor; and
    a stator having helical blades helically spaced apart on the stator, wherein the static gel strength test instrument characterizes gelation of a composition.

9. The static gel strength test instrument of claim 8, wherein the helical blades are helically spaced apart on a cylindrical surface on the stator.

10. The static gel strength test instrument of claim 8, wherein the rotor comprises a helical blade.

11. The static gel strength test instrument of claim 8, wherein the rotor comprises helical blades spaced apart from the helical blades of the stator by a substantially consistent gap.

12. The static gel strength test instrument of claim 8, wherein the rotor comprises helical blades, and wherein the helical blades of the rotor and the helical blades of the stator have a substantially same pitch.

13. The static gel strength test instrument of claim 8, wherein the rotor comprises helical blades, and wherein the helical blades of the rotor and the helical blades of the stator have a substantially same curvature.

14. A static gel strength test instrument, comprising:
   a stator comprising first helical blades helically spaced apart on the stator; and
   a rotor comprising a second helical blade.

15. The static gel strength test instrument of claim 14, wherein the first and second helical blades have a substantially same pitch.

16. The static gel strength test instrument of claim 14, wherein the first and second helical blades have a substantially same curvature.

17. The static gel strength test instrument of claim 14, wherein each of the first helical blades comprises a portion of a helix.

18. The static gel strength test instrument of claim 14, wherein the first helical blades are spaced apart from the second helical blade by a substantially consistent gap.

19. The static gel strength test instrument of claim 14, wherein the first helical blades are helically spaced apart on a cylindrical surface of the stator.

20. The static gel strength test instrument of claim 14, wherein the rotor comprises multiple second helical blades axially spaced apart on the rotor.

* * * * *